United States Patent [19]

Carroll

[11] Patent Number: 5,334,143
[45] Date of Patent: Aug. 2, 1994

[54] METHOD TO REMOVE COMMON BILE DUCT STONES

[76] Inventor: Brendon J. Carroll, 2278 Betty La., Beverly Hills, Calif. 90210

[21] Appl. No.: 869,730

[22] Filed: Apr. 17, 1992

[51] Int. Cl.$^5$ .......................................... A61M 31/00
[52] U.S. Cl. ...................................... 604/54; 604/102
[58] Field of Search ................. 604/51, 54, 96, 101, 604/102; 606/191, 192, 194, 127-128; 128/656-658; 600/16-18

[56] References Cited

U.S. PATENT DOCUMENTS

| | | | |
|---|---|---|---|
| 4,299,226 | 11/1981 | Banka | 128/657 X |
| 4,545,390 | 10/1985 | Leary | 128/772 |
| 4,577,637 | 3/1986 | Mueller, Jr. | 128/658 |
| 4,627,837 | 12/1986 | Gonzalo | 604/101 |
| 4,696,668 | 9/1987 | Wilcox | 604/28 |
| 4,771,776 | 9/1988 | Powell et al. | 606/194 |
| 4,909,258 | 3/1990 | Kuntz et al. | 128/658 |
| 4,943,275 | 7/1990 | Stricker | 600/18 |

Primary Examiner—C. Fred Rosenbaum
Assistant Examiner—Corrine Maglione

[57] ABSTRACT

A catheter device and method for laparoscopically dilating the sphincter muscle to flush common bile duct stones into the duodenum is set forth where the catheter consists of a flexible tube having three lumens. An inflatable balloon is carried by the flexible tube at its distal end and is inflatable and deflatable through an insufflation port. Radiopaque markers placed distally and proximally of the balloon are used to visualize the location of the balloon flouroscopically. A guidewire is advanced through the cystic duct, common bile duct and into the duodenum over which the catheter is advanced and the balloon positioned at the juncture of the common bile duct and duodenum. The balloon is then inflated sufficiently to dilate the sphincter muscle; the balloon is then deflated and the common bile duct irrigated with a fluid injected through an irrigation port located proximally of the balloon to flush the gallstones from the common bile duct.

8 Claims, 5 Drawing Sheets

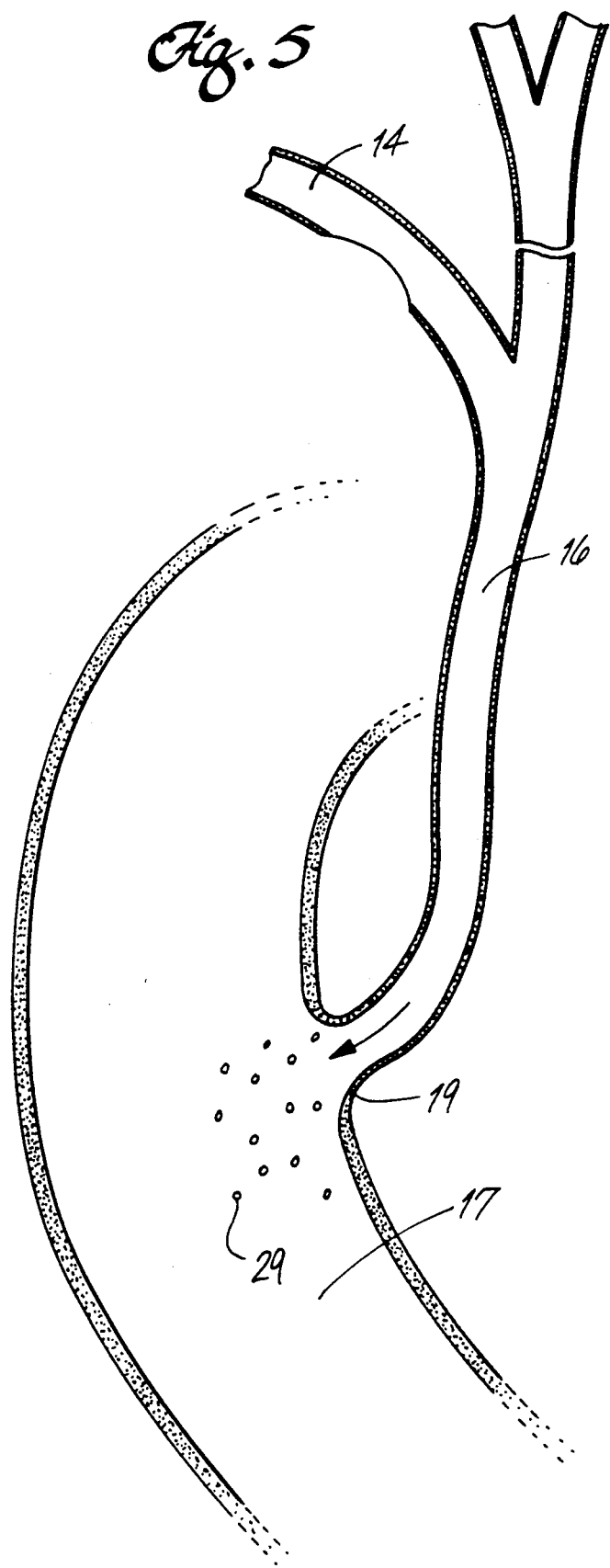

METHOD TO REMOVE COMMON BILE DUCT STONES

FIELD OF THE INVENTION

This invention relates to an inflatable balloon catheter to be used during laparoscopic trans-cystic common bile duct exploration to dilate the sphincter muscle at the distal end of the common bile duct to allow stones to pass through the duct and into the duodenum.

BACKGROUND OF THE INVENTION

In the performance of cholecystectomy surgery a certain percentage of patients who undergo the operation will have gallstones that have migrated from their gallbladder to the common bile duct. The stones may spontaneously pass through the distal end of the bile duct into the duodenum causing no harm or they may be trapped in the common bile duct by the sphincter muscle at the distal end of the duct. In the event the sphincter muscle gets irritated by the stones, the muscle will trap them and prevent them from passing into the duodenum. The trapping of the stones backs up the common bile duct thereby causing jaundice, pancreatitis and cholangitis.

Removal of the stones which had entered the common bile duct required that the surgeon make a large abdominal incision, remove the gallbladder, and then cut open the common bile duct. The surgeon would thereafter retrieve the stones one by one from the common bile duct by grasping the stones or using balloon catheters to pull them retrograde. Alternatively, the stones could be removed by resorting to endoscopic retrograde cholangiopancreatography-sphincterotomy (ERCP).

In retrieving the stones from the common bile duct by using the balloon catheters, the surgeon would extend the balloon portion of the catheter into the common bile duct beyond the stone, and thereafter inflate the balloon. The stone would then be withdrawn retrograde through the common bile duct and through the incision which was made in the common duct for inserting the catheter. In order for the choledochotomy incision in the common bile duct to heal properly, a T-tube was inserted in the common duct and left in place for approximately three weeks after the surgery which resulted in significant disability. The ERCP procedure to remove stones from the common bile duct required that an endoscope be passed through the patient's mouth, down through the stomach and into the duodenum. After identifying the ampulla of Vater, which is where the common bile duct drains into the duodenum, the endoscopist would then cannulate the ampulla and inject dye into the common duct retrograde and visualize the stones on fluorscopic x-ray. After the stones were found on x-ray, a cut was then made in the sphincter muscle in the distal bile duct from an instrument passed through the endoscope. By cutting the muscle, there was no longer a restriction to the flow of stones and the stones were therefore allowed to pass into the duodenum. This procedure involved an 8% morbidity and a 1% mortality risk to the patient most often due to severe pancreatitis.

A method for removing common duct stones laparoscopically has been used requiring a cholangiography to be first performed by passing a catheter through the cystic duct and then injecting dye into the common duct to visualize the stones flouorscopically. When the stones are identified in the common duct, a balloon dilating catheter is thereafter passed into the cystic duct and dilated sufficiently to permit the insertion of an endoscope through the cystic duct and into the common bile duct. By transcystic endoscopic common bile duct exploration, the stones are visually identified by the surgeon through the endoscope and thereafter grasped by a basket-type retriever and removed. There are limitations, however, to this procedure for transcystic common bile duct exploration. The procedure will fail if the cystic duct is too small to be dilated to sufficient size to allow the endoscope to enter into the common bile duct. In other cases, the stones may be too small to be grasped by the basket retriever. When stones of a very small diameter are stuck in the sphincter muscle at the distal end of the common bile duct, it is extremely difficult to retrieve the stones endoscopically.

Dilation of the sphincter muscle has been performed through the oral insertion of an endoscope that passed down through the stomach into the duodenum where the endoscope included a balloon means which was inserted retrograde into the common bile duct through the sphincter muscle. This technique resulted in an unacceptable complication rate which included complications such as pancreatitus and cholangitis.

Catheter devices in the prior art which utilize balloons in the removal of common bile duct stones used the balloons for withdrawing stones retrograde or blocking passages. In U.S. Pat. No. 4,725,264, entitled "Double Barreled Biliary Balloon Catheter" a catheter was designed to remove gallstones which had obstructed the common bile duct. The catheter balloon was attached to a filiform probe which had passed beyond the stones and the catheter balloon was then positioned beneath the stone, inflated and the entire assembly was then drawn upwardly until the stone had fallen out of the encised opening in the common duct. Similarly, in U.S. Pat. No. 4,627,837, entitled "Catheter Device", the catheter device was equipped with a pair of balloons which were inflatable from the proximal end of the catheter where one balloon acted as an anchor to retain the catheter in the ampulla and a second balloon was inflated beneath the stone and the stone withdrawn retrograde and removed through the choledochotomy incision. A double lumen catheter is descibed in U.S. Pat. No. 4,919,651, having a balloon at one end and a bifurcated inlet connector at the other for the controlled filling of the biliary ductal system with a dilute dye for operative cholangiography. In this device, the catheter was drawn retrograde until the expanded balloon impinged upon and sealed an opening.

An internal mammary artery catheter is shown in U.S. Pat. No. 4,909,258 for performing selective arteriography or angioplasty on internal mammary or artery graft. The catheter utilizes a balloon and a proximal port. The port delivers an anglographic dye for visualizing vascular obstructions to the internal mammary artery or graft within the subclavian artery. The catheter is inserted over a guidewire into the subclavian artery and the balloon inflated at a point distal to the junction of the subclavian artery and the internal mammary artery. The balloon is inflated to obstruct blood flow to an axillary artery and thereafter an angiographic dye is injected through the proximal port for visualizing the angiographic dye using radiography. Thus, the catheters of the prior art have utilized a balloon for the purpose of removing stones from the common bile duct by retrograde movement of the balloon to pull the stone back through the incision in the common duct. In some instances, this procedure required the installation of a T-tube which was left in place for a period of at least 3 weeks after the surgery. Other procedures of the prior art required that a cut be made in the sphincter muscle in the distal bile duct by utilizing an instrument passed through an endoscope. By cutting the sphincter muscle the patient was exposed to the risk of severe pancreatitis with the possibility of serious morbidity and even mortality.

SUMMARY OF THE INVENTION

There is, therefore, provided according to the present invention, a catheter device and method for laparoscpically dilating the sphincter muscle and thereafter flushing the common bile duct stones into the duodenum.

The present invention is directed to a catheter which is composed of a flexible tube having an arcuate distal end to promote passage of the catheter into the cystic duct and thereafter into the common bile duct. The flexible tube contains a first, second and third lumen extending axially therein and an opening at the distal end of the flexible tube which communicates with the first lumen and with a first inlet port located at the proximal end of the flexible tube. An insufflation port communicates with the second lumen and a second inlet port to permit the passage of gas for the inflation of an inflatable balloon which sealingly encloses the flexible tube at its distal end. To easily accommodate the passage of the catheter through the cystic duct and into the common bile duct, the inflatable balloon is so dimensioned and proportioned that the distal end of the flexible tube retains its curvature while the balloon remains deflated and also when the balloon is inflated to dilate the sphincter muscle.

The flexible tube has an irrigation port which is located proximally of the balloon. The irrigation port communicates with the third lumen and a third inlet port to permit irrigation by a saline or idonated fluid, or a solvent such as methyl terbutyl ether in which the gallstones could be dissolved into small particles, to flush the common bile duct after the sphincter muscle has been dilated and the balloon deflated. To visualize the common bile duct before and after dilation of the balloon, radiopaque markers are used to deliniate the distal and proximal ends of the balloon and a third radiopaque marker is used to identify the location of the proximal irrigation port such that the balloon may be positioned flouroscopically within the common bile duct before the sphincter muscle is dilated. After the sphincter muscle is dilated, the balloon is deflated and the bile duct is visualized flouroscopically by the location of the radiopaque markers.

The method for laparoscopically removing stones captively held in the common bile duct incorporates the steps of inserting an atraumatic guidewire through the cystic duct, through the common bile duct and into the duodenum, and thereafter advancing the catheter over the guidewire by passage of the wire through the first lumen and distal opening of the flexible tube. The catheter is advanced over the wire until the first and second radiopaque markers defining the axial dimension of the balloon are flourscopically visualized within the common bile duct and the catheter thereafter positioned at the distal end of the common bile duct for dilation of the sphincter muscle. The balloon is then sufficiently inflated to dilate the sphincter muscle and then deflated.

An iodinated fluid is thereafter admitted into the common bile duct by passage through the third lumen and the irrigation port to flush the stones into the duodenum. In some instances, it may not be possible to pass the distal end of the catheter through the cystic duct because of the small size of the duct. When this situation is encountered, the balloon may be dilated first in the cystic duct to accommodate passage of the catheter into the common bile duct.

BRIEF DESCRIPTION OF THE DRAWINGS

These and other features and advantages will become appreciated as the same become better understood with reference to the following specification, claims and drawings wherein:

FIG. 5 is an illustration of the cystic duct, common bile duct and juncture of the common bile duct with the duodenum after the sphincter muscle has been dilated and the catheter withdrawn.

FIG. 6 is a cross-sectional view of the catheter device taken along the line 6—6.

DETAILED DESCRIPTION

Figure 1:
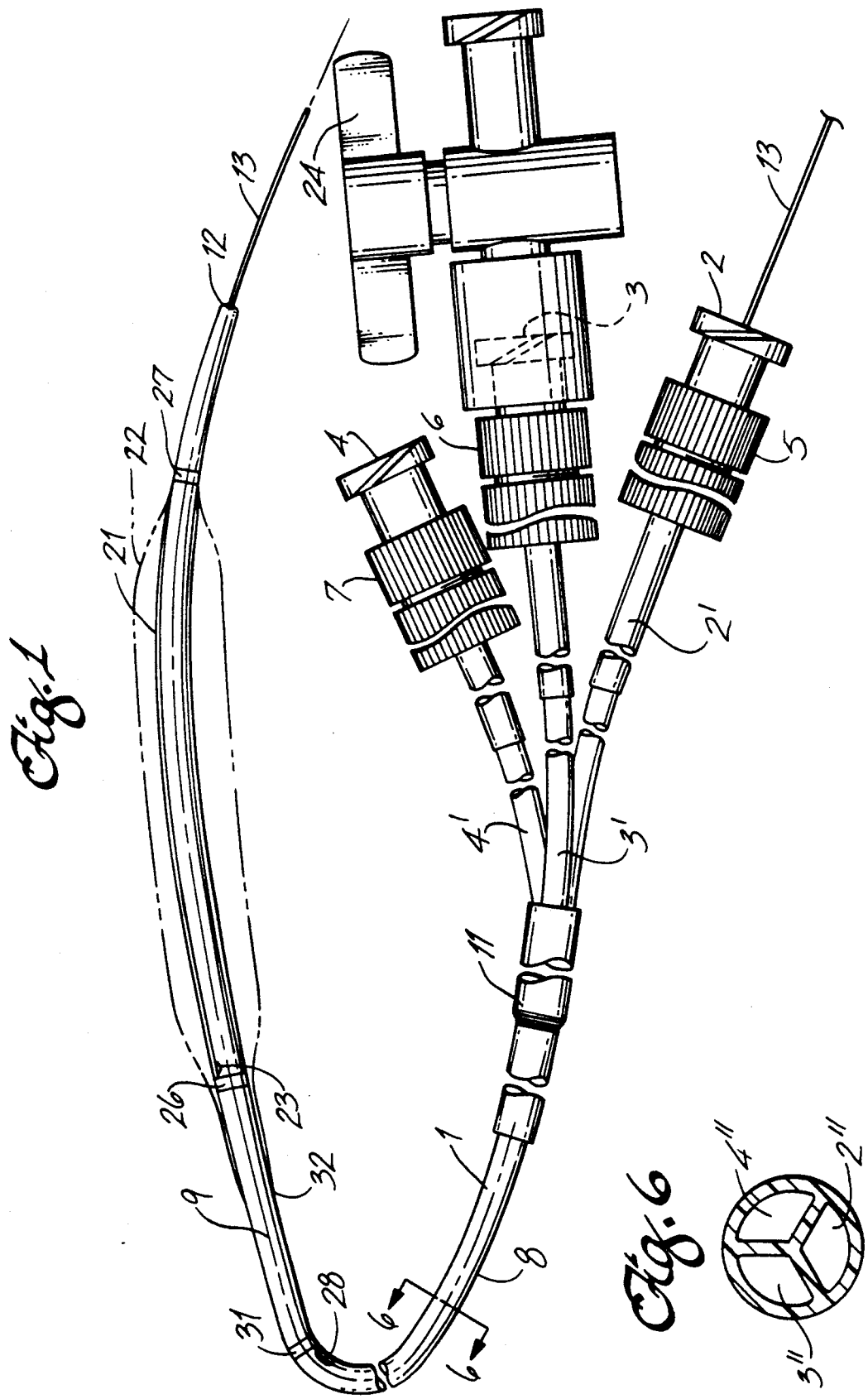
FIG. 1 is a perspective view of the catheter device of this invention.

Referring to FIG. 1, the catheter device 1 of this invention is shown in perspective. As can be seen in FIG. 1, the catheter 1 has a first inlet port 2, a second inlet port 3 and a third inlet port 4 which are associated respectively with fitting 5, fitting 6, and fitting 7. A flexible tube 8 having an axis of elongation 9 contains three axially extending lumens shown in FIG. 6 which is a cross-section of flexible tube 8. Flexible tube 8 is preferably made of a plastic material which has the physical property of having sufficient rigidity to be formed into segments of preselected curvature.

Referring to both FIG. 6 and FIG. 1, it can be seen that first inlet port 2 communicates with inlet conduit 2' which in turn communicates with first lumen 2" and similarly second inlet port 3 communicates with second inlet conduit 3' which in turn communicates with second lumen 3"; the third lumen 4" communicates with the third inlet port 4 through inlet conduit 4'. Thus, the catheter device 1 of this invention contains three separate inlet conduits which have a proximal confluence 11 with flexible tube 8 such that each one of the lumens contained within flexible tube 8 directly communicates with a respective inlet port thereby defining three separate and distinct passageways.

Figure 2:
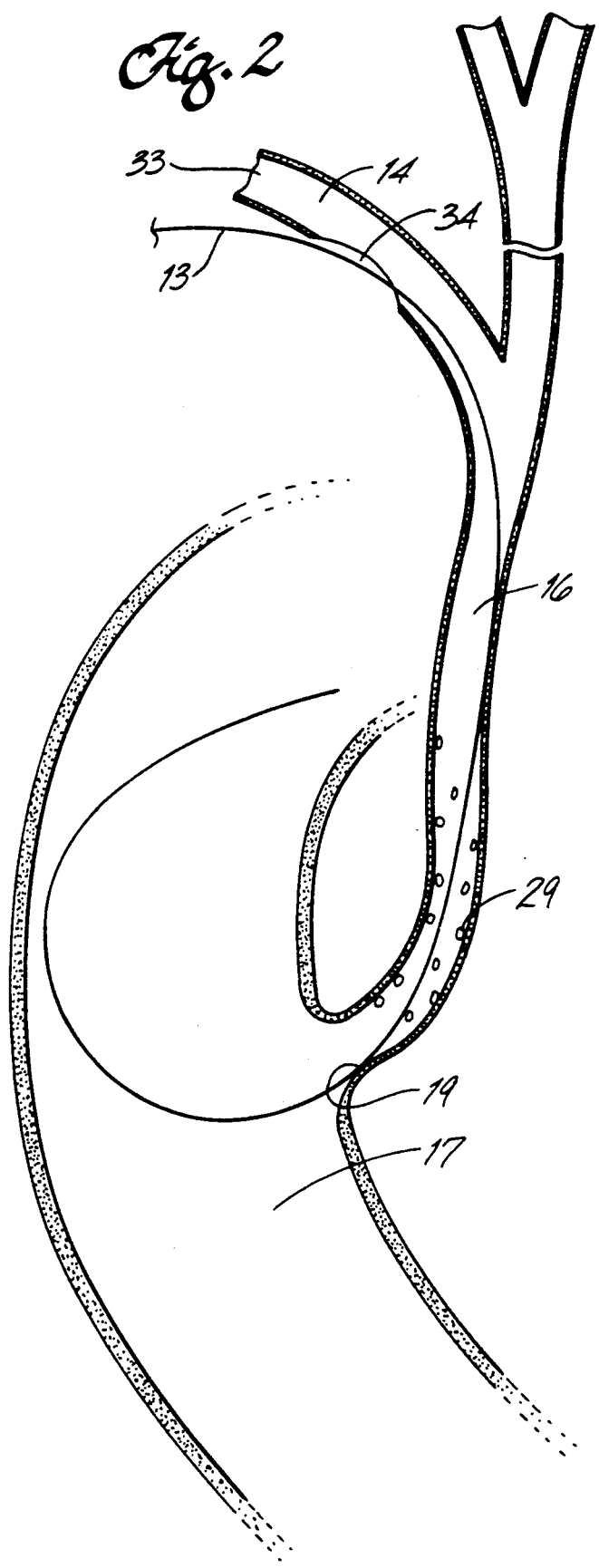
FIG. 2 is a secional view illustrating the cystic duct, common bile duct and the juncture of the common bile duct with the duodenum.
Figure 3:
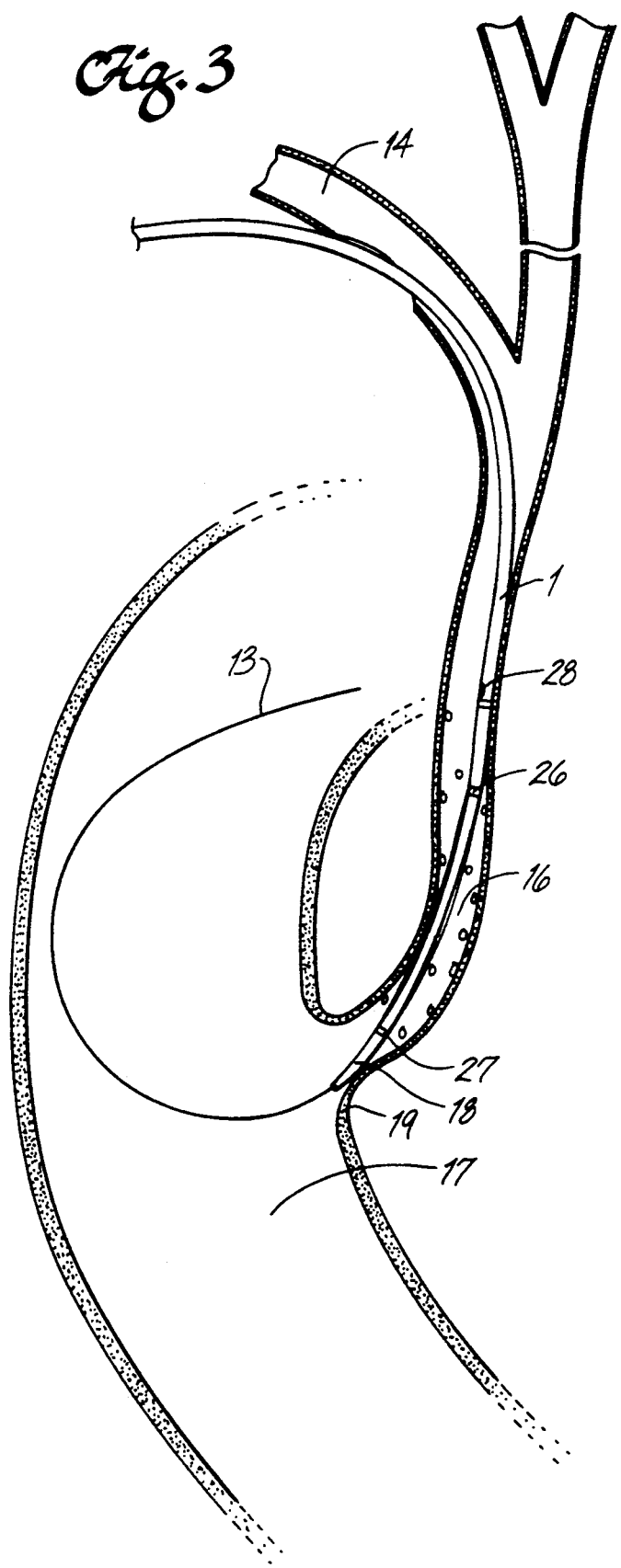
FIG. 3 is a cross-sectional view of the cystic duct, common bile duct and juncture of the common bile duct with the duodenum and illustrates the insertion of the catheter through the cystic duct and into the common bile duct with the inflatable balloon positioned for dilating the sphincter muscle.

To advance the catheter 1 of this invention through the cystic duct and into the common bile duct juncture with the duodenum, catheter device 1 has a distal opening 12 which communicates with the first lumen 2"; thus, after guidewire 13 is flouroscopically guided through the cystic duct and common bile duct into the duodenum, the catheter may be advanced along guidewire 13 for selective positioning. FIG. 2 illustrates the guidewire 13 passing through the cystic duct 14 and the common bile duct 16 and into the duodenum 17; FIG. 3 illustrates the advancement of the catheter device 1 over the guidewire 13 with distal end 18 of the catheter 1 device extending in part into the duodenum 17. Because of the abrupt curvature of the common bile duct 16 proximally of the juncture 19 of the common bile duct with the duodenum, the catheter device has a preselected fixed distal curvature which is shown in FIG. 3 and can more clearly be seen in FIG. 1.

Figure 4:
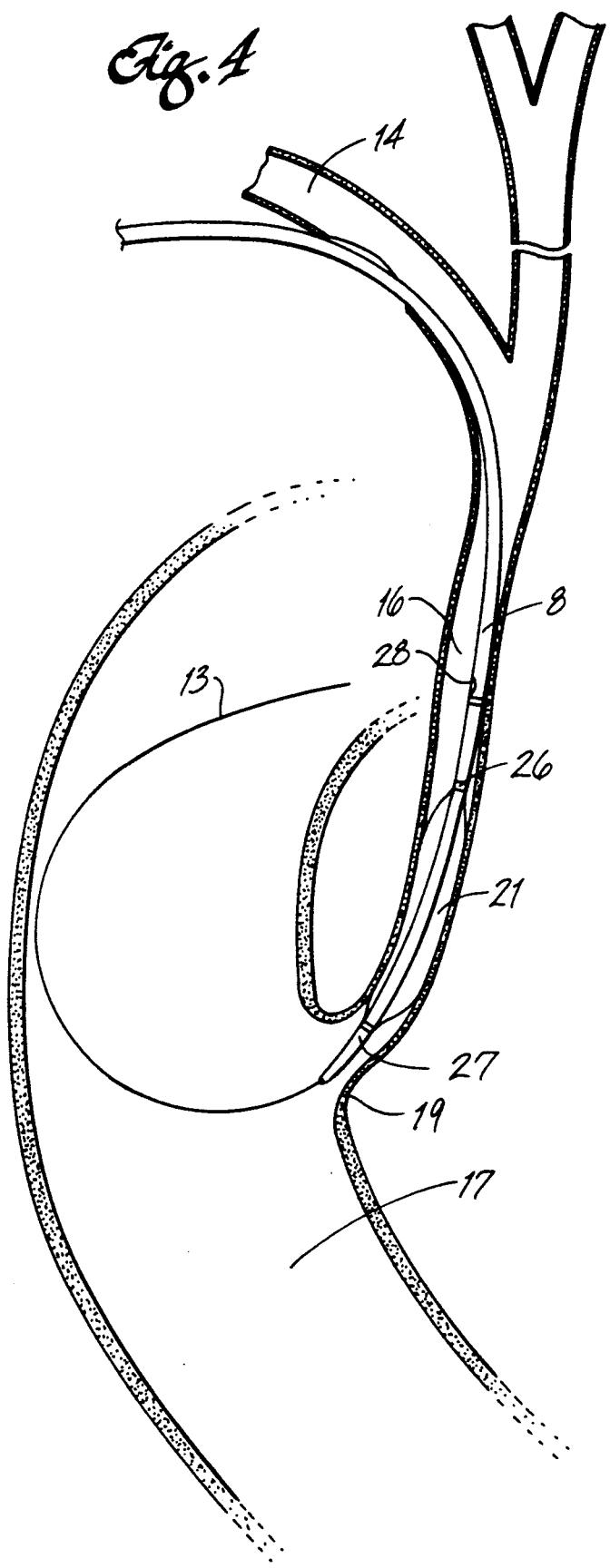
FIG. 4 is an illustration of the cystic duct, common bile duct and juncture of the common bile duct with the duodenum with the inflatable balloon inflated and the sphincter muscle expanded.

To dilate the sphincter muscle which is located within the common bile duct at the juncture 19 of the common bile duct with the duodenum, an inflatable balloon 21 which is sealed at its distal and proximal ends by an appropriate bonding method of the flexible tube 8 is utilized and located adjacent the distal end of the catheter. FIG. 1 illustrates balloon 21 in a deflated mode and also in the inflated mode 22 where the inflated mode is shown in phantom lines. In both the deflated mode 21 and inflated mode 22 of the inflatable balloon, the curvature of the distal end of the catheter is retained by sufficient rigidity of the flexible tube distal end. This permits uniform dilation of the sphincter muscle when the balloon is inflated as shown in FIG. 4.

To inflate inflatable balloon 21, flexible tube 8 has an insufflation port 23 which communicates with and is located at the terminal end of the distal end of the second lumen 3". Insufflation port 23 is sealingly enclosed by the balloon and communicates with the second inlet port 3 which in turn is connected to a meter valve 24 through which sufficient CO2 gas may be metered by the surgeon to attain a predetermined pressure within the balloon to dilate the sphincter muscle. To delinate the axial dimensions of the balloon flouroscopically, a proximal radiopaque marker 26 is utilized along with a distal radiopaque marker 27; thus, the balloon may be positioned flouroscopically within the common bile duct and extending in part into the duodenum before the balloon is inflated.

The third lumen 4" communicates with irrigation port 28 to permit irrigation by a saline or iodinated fluid or in another method, irrigation by a solvent such as Methyl Terbutyl Ether in which the gallstones 29 may be dissolved into smaller stones and flushed from the common bile duct after the sphincter muscle is dilated and the irrigation balloon deflated. Irrigation port 18 is located proximally of a third radiopaque marker 31; radiopaque marker 31 permits visualization of the irrigation port during the irrigation process flouroscopically. Radiopaque markers 26 and 27 are recommended to be approximately 5 cm apart and radiopaque marker 31 is recommended to be approximately 1.5 cm from the distal end 32 of inflatable balloon 21.

FIGS. 2, 3, 4 and 5 illustrate the method of use of the catheter device of this invention. As is shown in FIG. 2, the atraumatic guidewire 13 is inserted into cystic duct 14 after a cholecystectomy has been performed which permits insertion of a guidewire 13 at the incised end 33 of the cystic duct or through the incision 34 as illustrated in FIG. 2. To reach the duodenum, guidewire 13 is advanced through the cystic duct, through the common bile duct 16 and through the junction 19 of the common bile duct with the duodenum.

As can also be seen in FIG. 2, the gallstones 29 are captively held in the common bile duct by the sphincter muscle. To dislodge the gallstones 29 from the common bile duct, the catheter device 1 is advanced over atraumatic guidewire 13 as shown in FIG. 3, and positioned by visualizing the radiopaque markers 26 and 27 flouroscopically. The stones may thereafter be visualized floursocopically by irrigating the common bile duct through irrigation port 28. By dilating the sphincter muscle as shown in FIG. 4 by inflating inflatable balloon 21, the gallstones held captively within the common bile duct will be allowed to pass spontaneously into the duodenum or thereafter flushed into the doudenum by irrigation of the common bile duct.

In some instances, the anatomy of the patient is such that the catheter is unable to advance over guidewire 13 through the cystic duct; when this situation occurs, the inflatable balloon 21 may be positioned within the cystic duct by flouroscopic visualization and thereafter inflated to dilate the cystic duct and thereby permit passage of the catheter into the common bile duct.

An alternative method of removing gallstones from the common bile duct utilizes a solvent such as Methyl Terbutyl Ether to dissolve the gallstone into small particles for flushing from the common bile duct. In utilizing this method, the inflatable balloon is inflated sufficiently to dilate the sphincter and the solvent is then injected through irrigation port 28 into the common bile duct and held for a sufficient period of time to dissolve the stones. The solvent may thereafter be used after the balloon is deflated to irrigate the common bile duct and pass harmlessly into the duodenum.

While I have shown and described an ampula dilating catheter and method to remove common bile duct stones, it is to be understood that it is subject to many modifications without departing from the scope and spirit of the claims as recited herein.

What is claimed is:

1. A method for laparoscopically removing stones captively held in the common bile duct comprising the steps of:
   a) advancing a guidewire laparoscopically through the cystic duct and through the common bile duct and extending said guidewire into the duodenum;
   b) advancing a flexible catheter having an axis of elongation over said guidewire, said catheter having sufficient distal curvature to enable the passage of the distal end of said catheter through the cystic duct junction with said common bile duct, said catheter having an inflatable balloon adjacent said distal end where said inflatable balloon has first and second radiopaque markers defining the axial boundries of said balloon and an irrigation port located proximally of said balloon, said irrigation port having a third radiopaque marker located proximally of said first and second radiopaque markers and adjacent said irrigation port;
   c) visualizing the passage of said inflatable balloon through said cystic duct and into said common bile duct flouroscopically;
   d) positioning said balloon adjacent the juncture of said common bile duct and duodenum to permit dilation of the sphincter muscle;
   e) inflating said balloon sufficiently to dilate said sphincter muscle;
   f) deflating said balloon; and
   g) irrigating said common bile duct with a fluid to flush said stones into said duodenum.

2. The method recited in claim 1 wherein said flexible tube has sufficient distal rigidity to retain said curvature when said inflatable balloon is inflated such that said sphincter muscle is uniformly dilated.

3. The method recited in claim 2 further comprising the step of inflating said balloon to dilate the cystic duct and deflating said balloon to permit passage of said catheter into said common bile duct.

4. The method recited in claim 1 wherein said irrigating fluid is methly terbutyl ether.

5. A method for laparoscopically removing gallstones captively held in the common bile duct comprising the steps of:
   a) advancing a guidewire laparoscopically through the cystic duct and through the common bile duct and extending said guidewire into the duodenum;
   b) advancing a flexible catheter having an axis of elongation over said guidewire, said catheter having sufficient distal curvature to enable the passage of the distal end of said catheter through the cystic duct junction with said common bile duct, said catheter having an inflatable balloon adjacent said distal end where said inflatable balloon has first and second radiopaque markers defining the axial boundries of said balloon and an irrigation port located proximally of said balloon, said irrigation port having a third radiopaque marker located proximally of said first and second radiopaque markers and adjacent said irrigation port;
   c) visualizing the passage of said inflatable balloon through said cystic duct and into said common bile duct flouroscopically;
   d) positioning said balloon adjacent the juncture of said common bile duct and duodenum to permit dilation of the sphincter muscle;
   e) inflating said balloon sufficiently to dilate said sphincter muscle;
   f) injecting a solvent through said irrigation port into the common bile duct to sufficiently dissolve said gallstones;
   g) deflating said inflatable balloon;
   h) irrigating said common bile duct with a fluid to flush said common bile duct.

6. The method recited in claim 5 wherein said flexible tube has sufficient distal rigidity to retain said curvature when said inflatable balloon is inflated such that said sphincter muscle is uniformly dilated.

7. The method recited in claim 6 further comprising the step of inflating said balloon to dilate the cystic duct and deflating said balloon to permit passage of said catheter into said common bile duct.

8. The method recited in claim 5 wherein said solvent is methyl terbutyl ether.

* * * * *